United States Patent [19]
Prasad

[11] Patent Number: 4,483,821
[45] Date of Patent: Nov. 20, 1984

[54] COBALT-CHROMIUM DENTAL ALLOYS

[75] Inventor: Arun Prasad, Cheshire, Conn.

[73] Assignee: Jeneric Industries, Inc., Wallingford, Conn.

[21] Appl. No.: 453,135

[22] Filed: Dec. 27, 1982

[51] Int. Cl.³ .............................................. C22C 19/07
[52] U.S. Cl. .................................... 420/437; 420/588
[58] Field of Search ............... 420/437, 588; 148/408, 148/419, 425, 442

[56] References Cited

U.S. PATENT DOCUMENTS 4,382,909  5/1983  Zwingmann ........................ 420/437

Primary Examiner—R. Dean
Attorney, Agent, or Firm—Barry Kramer

[57] ABSTRACT

A cobalt-chromium alloy consisting essentially

| Element | Weight Percent |
|---------|----------------|
| Cobalt | 40–60 |
| Chromium | 20–35 |
| Tungsten | 10–20 |
| Gallium | 3–10 |
| Rhenium | 0.1–1.0 | and from 1 to about 1.75% aluminum, said alloy constituents totalling 100%. These alloys exhibit outstanding physical properties and can be used advantageously as a substitute for precious metals and alloys thereof as well as nickel-chromium-based alloys in the fabrication of porcelain-veneered fixed bridgework and crowns.

4 Claims, 1 Drawing Figure

COBALT-CHROMIUM DENTAL ALLOYS

FIELD OF THE INVENTION

This invention relates to cobalt-chromium dental alloys. More particularly, this invention relates to cobalt-chromium alloys containing aluminum, tungsten, gallium and rhenium such that the resulting alloys exhibit outstanding physical and thermal properties thereby rendering such alloys suitable for use in the fabrication of porcelain-fused-to-metal restorations.

BACKGROUND OF THE INVENTION

Numerous criteria must be met by an alloy to be used in the fabrication of prosthetic dental appliances such as porcelain-veneered fixed bridgework and crowns. The alloy must be tissue tolerant, tarnish resistant, corrosion resistant and non-toxic. In addition, any oxide formed on the alloy surface should be adherent and not grow dramatically in thickness during the porcelain-fixing cycle. The oxides formed must also be compatible with the porcelain; otherwise, they may affect the thermal expansion of the interfacial porcelain. Still further, the oxides should not discolor the porcelain. The alloy must also have a coefficient of thermal expansion slightly higher than that of the porcelains currently available on the market thereby placing the porcelain under compression and minimizing the stresses formed at the interface.

The alloy also should be shape-stable with porcelain application, possess adequate strength for function, produce an acceptable fit and be solderable. Finally, it should possess a high modulus of elasticity, high-yield strength and hardness and be easily cast, ground and polished using techniques conventionally employed in dental laboratories. The criteria which govern the selection of a suitable alloy for use in the preparation of porcelain-veneered fixed bridgework and crowns are quite different from the criteria involved in selecting alloys for use in the fabrication of partial dentures which generally are not used in conjunction with porcelain.

These criteria, to a large extent, have heretofore been met by precious alloys containing gold, platinum, palladium, silver, indium, tin, gallium, zinc, and the like, and trace metals, such as those set forth in U.S. Pat. Nos. 1,283,264, 3,413,723, 3,667,936, 3,767,391, 3,819,366, 3,981,723 and 4,007,040 and the like.

With the ever increasing and fluctuating cost of precious metals and the superior physical properties and technological advantages offered by nickel-chromebase alloys, such alloys have become widely used as an alternative to precious alloys in dentistry. These alloys generally utilize tin, gallium and the like to impart specific physical characteristics. Typical of such alloys are those described in U.S. Pat. Nos. 2,089,587, 3,304,177, 3,464,817, 3,749,570 and 3,914,867.

Currently, there is growing concern about nickel being an allergen and beryllium being a toxic element. Although much data are still needed, there is an apparent need for a non-precious alloy which contains neither nickel nor beryllium and yet meets the above criteria. A number of cobalt-chromium base alloys with and without nickel and/or beryllium have heretofore been employed in dentistry for the fabrication of removable partials, crowns and bridgework. Typical of such alloys are those described in U.S. Pat. Nos. 3,756,809, 3,802,875, 3,802,934 and 3,837,838. However, their compositions and physical and thermal properties have limited their use for porcelain-veneered crown and bridgework. Cobalt-chromium based alloys having a variety of compositions and said to be useful for procelain-fused-to-metal restorations have been disclosed in U.S. Pat. Nos. 4,229,215, 4,253,869, 4,255,190 and 4,263,045.

SUMMARY OF THE INVENTION

Accordingly, it is an object of the present invention to provide a non-precious alloy which exhibits many of the properties of precious metal alloys heretofore considered desirable in the fabrication of porcelain-veneered fixed bridgework and crowns.

It is another object of the present invention to provide a non-precious alloy free of nickel and/or beryllium.

These as well as other objects and advantages are accomplished by the present invention which provides chromium-cobalt alloys which are significantly different from prior chromium-cobalt alloys heretofore employed in the fabrication of prosthetic dental appliances. The chromium-cobalt alloys of the present invention exhibit melting characteristics enabling the use of standard natural gas/oxygen torches conventionally used in dental laboratories. Moreover, the alloys of the present invention exhibit greatly improved oxidation resistance thereby facilitating the formation of a tenacious bond with porcelain. Accordingly, the alloys of the present invention can be successfully employed in the fabrication of porcelain-veneered fixed bridgework and crowns in lieu of the precious metal and nickel-chromium-base alloys heretofore employed.

The cobalt-chromium alloys of the present invention consist essentially of:

| Element | Weight Percent |
| --- | --- |
| Cobalt | 40–60 |
| Chromium | 20–35 |
| Tungsten | 10–20 |
| Gallium | 3–10 |
| Rhenium | 0.1–1.0 | and from about 1 to about 1.75% aluminum, said alloy constituents totalling 100%. These alloys exhibit outstanding physical properties and can be used advantageously as a substitute for precious metals and alloys thereof as well as nickel-chromium-based alloys in the fabrication of procelain-veneered fixed bridgework and crowns.

In addition, the alloy can contain yttrium to improve the grain structure, the grain boundary characteristics and oxidation resistance. The alloy can contain yttrium in an amount up to about 0.25%.

Preferably, the cobalt-chromium alloys of the present invention consist essentially of:

| Element | Percent by Weight |
| --- | --- |
| Cobalt | 40–55 |
| Chromium | 20–35 |
| Tungsten | 14–17 |
| Gallium | 4–6 |
| Rhenium | 0.4–0.6 | and from about 1 to about 1.5% aluminum, said alloy constituents totalling 100%.

DESCRIPTION OF THE PREFERRED EMBODIMENTS

Figure 1:
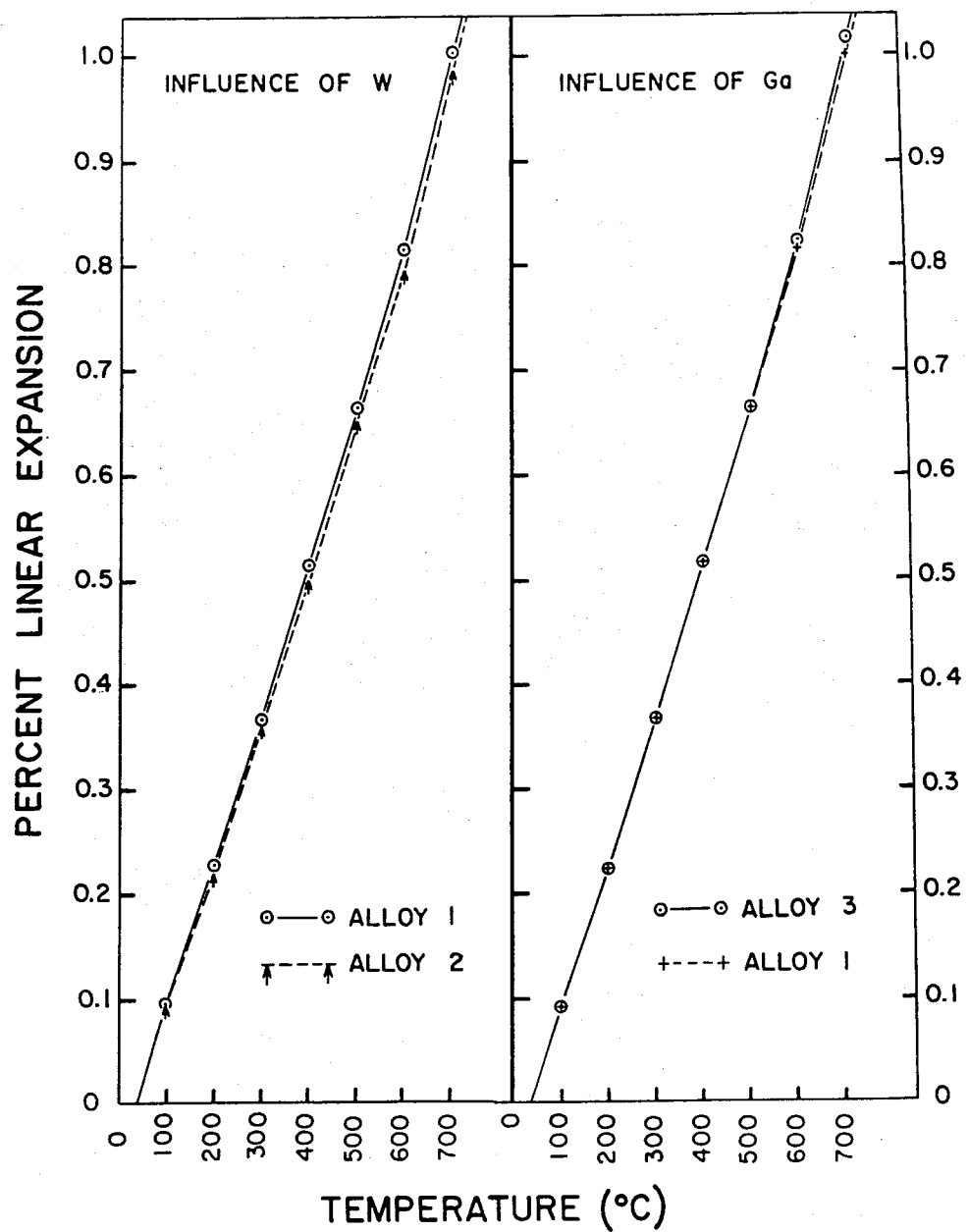
FIG. 1 shows the thermal expansion behavior of the alloys of this invention with changes in the concentration of tungsten and gallium. The compositions of the 5 alloys are given below in Table I.

The cobalt-chromium alloys of the present invention are especially suited for use in the fabrication of prosthetic dental appliances since the cobalt in the alloy imparts characteristics to the alloy which closely correspond with that of precious metals, especially the coefficient of thermal expansion which is quite close to that of gold. The chromium in the alloy provides enhanced corrosion and tarnish resistance. Chromium in amounts of from about 20% to 35% acts as a solid solution strengthener and provides a convenient means of adjusting the thermal expansion characteristics of the alloy to conform to the variations encountered upon use of different commercial porcelains.

The coefficient of thermal expansion of the alloy also depends upon the concentrations of tungsten, rhenium, aluminum and gallium. Tungsten and rhenium lower the coefficient of thermal expansion; aluminum and gallium, on the other hand, increase the coefficient of thermal expansion, although to a lesser extent.

The gallium, in addition to changing the coefficient of thermal expansion, also lowers the melting point of the alloy and provides an oxide which will not discolor the porcelain. Similarly, rhenium has an additional function, in this case providing added strength to the alloy.

It has been found in accordance with the present invention that the amount of aluminum employed in the present cobalt-chromium alloys helps in meeting the various criteria imposed on alloys which are useful in the preparation of porcelain-veneered fixed bridgework and crowns. In particular, it has been found that porcelain readily and firmly bonds to the alloys of the present invention having the prescribed aluminum content. Also, the aluminum lowers the casting temperature and enhances the oxidation resistance of the alloy. This increased oxidation resistance helps prevent the formation of a thick oxide layer on the casting during the porcelain application process. This is important because thick oxide layers are fragile and impair the strength of the porcelain-metal bond in porcelain-fused-to-metal dental restorations.

The castings obtained with the alloys of the present invention exhibit smooth non-porous surfaces. Moreover, the lower casting temperatures for these alloys result in less interaction with the commercially available investments, thereby enabling the fabrication of less porous castings.

The alloys of the present invention can be prepared by conventional alloying techniques. If desired, alloying can be done in air, under vacuum or by employing a blanket of an inert gas such as argon. The latter precautions, although preferred, are not considered essential. Generally, the major alloy constituents are melted first, such as through use of an induction furnace, taking care to maintain a homogeneous distribution of chromium in the melt by overcoming its tendency to float to the surface. After the cobalt and chromium have been melted and are well dispersed, tungsten can be added. Thereafter, the remaining alloy constituents can be added in either elemental form or as a preformed alloy with cobalt or chromium. Once the alloy melt is prepared and ingots cast therefrom, the remelting of the alloy ingot may be accomplished using a standard natural gas/oxygen torch or induction melting equipment.

The alloys of the present invention can be used instead of precious metals and nickel-chrome/base alloys without requiring any significant changes in technique other than as presently practiced in a dental laboratory. The absence of nickel and beryllium precludes the need for any special handling precautions.

The following examples further illustrate the criticalities of the alloy composition of the present invention. Unless otherwise specified, all percentages and parts are by weight.

EXAMPLES 1-3

The alloy compositions set forth in Table I were prepared in the manner set forth above:

TABLE I

| Alloy | Co | Cr | W | Ga | Re | Y | Al |
|---|---|---|---|---|---|---|---|
| 1 | 54.15 | 25.0 | 15.0 | 4.0 | 0.5 | 0.1 | 1.25 |
| 2 | 52.15 | 25.0 | 17.0 | 4.0 | 0.5 | 0.1 | 1.25 |
| 3 | 52.15 | 25.0 | 15.0 | 6.0 | 0.5 | 0.1 | 1.25 |

FIG. 1 shows the thermal expansion behavior of these alloys over a temperature range from 30° C. to 700° C. The percentage expansion data shown was measured using a Theta differential dilatometer, where the reference temperature was 30° C., the rate of temperature climb was 3° C./minute and the reference standard was pure platinum. As shown in this figure, varying the concentration of tungsten and to some extent gallium changes the thermal expansion of the alloy. In terms of porcelain-fused-to-metal restorations, this allows one to choose an alloy having a thermal expansion which is greater than the thermal expansion of the porcelain. In practice, this ability to tailor the coefficient of expansion of the alloy to a variety of porcelains while still maintaining the alloy's oxidation resistance and functional properties make the alloys of this invention particularly suitable for porcelain-fused-to-metal restorations.

Table II shows the physical properties—specifically the tensile strength and elongation—of the alloys of Table I. These values were determined using an Instron machine. All of the values are within the range which is suitable for porcelain-fused-to-metal restorations.

TABLE II

| Alloy | Yield Strength | Ultimate Tensile Strength | Elongation |
|---|---|---|---|
| 1 | 74,000 | 104,000 | 10% |
| 2 | 100,000 | 112,000 | 5% |
| 3 | 90,000 | 110,000 | 6% |

In addition to their physical and thermal expansion characteristics, each of the alloys in Table I was found to have an oxide coating especially suitable for bonding to porcelain.

Although specific embodiments of the invention have been described and illustrated, it is to be understood that modifications can be made without departing from the invention's spirit and scope. Thus the concentrations of cobalt, chromium, tungsten, gallium, rhenium and aluminum can be varied from the percentages illustrated and alloys having the superior characteristics of the invention will still result. For example, the cobalt concentration can be varied at least between 40 and 60%, the chromium concentration between 20 and 35%; the tungsten concentration between 10 and 20%; the gallium concentration between 3 and 10%; the rhenium concentration between 0.1 and 1%; and the aluminum concentration between 1 and 1.75%.

What is claimed is:

1. A cobalt-chromium dental alloy for use is porecelain-fused-to-metal restorations consisting essentially of about:

| Element | Weight Percent |
|---------|----------------|
| Cobalt | 40–60 |
| Chromium | 20–35 |
| Tungsten | 10–20 |
| Gallium | 3–10 |
| Rhenium | 0.1–1.0 | and from about 1 to about 1.75% aluminum.

2. A cobalt-chromium dental alloy for use in porecelain-fused-to metal restorations consisting essentially of about:

| Element | Percent by Weight |
|---------|-------------------|
| Cobalt | 40–55 |
| Chromium | 20–35 |
| Tungsten | 14–17 |
| Gallium | 4–6 |
| Rhenium | 0.4–0.6 | and from about 1 to about 1.5% aluminum.

3. A cobalt-chromium dental alloy as defined in claim 1 additionally containing yttrium in an amount up to about 0.25%.

4. A cobalt-chromium dental alloy as defined in claim 2 additionally containing yttrium in an amount up to about 0.25%.

* * * * *